United States Patent [19]

Murad et al.

[11] Patent Number: 4,474,892

[45] Date of Patent: Oct. 2, 1984

[54] TWO-SITE IMMUNOASSAYS USING MONOCLONAL ANTIBODIES OF DIFFERENT CLASSES OR SUBCLASSES AND TEST KITS FOR PERFORMING SAME

[75] Inventors: Ferid Murad, Los Altos Hills; John A. Lewicki, San Jose, both of Calif.

[73] Assignee: Board of Trustees of The Leland Stanford Junior University, Stanford, Calif.

[21] Appl. No.: 466,798

[22] Filed: Feb. 16, 1983

[51] Int. Cl.$^3$ .................... G01N 33/54; G01N 33/56
[52] U.S. Cl. .................... 436/513; 436/519; 436/548; 436/804; 436/808; 436/819; 436/828; 436/824
[58] Field of Search ............ 436/513, 519, 548, 804, 436/808, 819, 824, 828

[56] References Cited

U.S. PATENT DOCUMENTS

| | | | |
|---|---|---|---|
| 3,645,852 | 2/1972 | Axen et al. | 435/7 |
| 3,654,090 | 4/1972 | Schuurs et al. | 435/7 |
| 3,867,517 | 2/1975 | Ling | 436/531 |
| 3,940,475 | 2/1976 | Gross | 436/518 |
| 4,098,876 | 7/1978 | Piasio et al. | 436/527 |
| 4,174,384 | 11/1979 | Ullman et al. | 436/532 |
| 4,376,110 | 3/1983 | David et al. | 436/513 |

FOREIGN PATENT DOCUMENTS

| | | | |
|---|---|---|---|
| 0889855 | 4/1982 | Belgium | 436/513 |
| 2487983 | 5/1982 | France | 436/513 |

OTHER PUBLICATIONS

Handbook of Radioimmunoassay, 1977, pp. 131–154.
Methods in Enzymology, 1980, 70:334–355.
Sevier et al., Clin. Chem., 27, (1981), 1797–1806.
Ex et al., Immunochemistry, 15, (1978), 429–436.
Dewitt et al., J. Biol. Chem., 256, (1981), 10375–82.
Shimizu et al., Clin. Chem., 28, (1982), 546–7.
Ehrlich et al., J. Immunol., (1982).
Potocnjak et al., Science, 215, (1982), 1637–9.

*Primary Examiner*—Christine M. Nucker
*Attorney, Agent, or Firm*—Ciotti & Murashige

[57] ABSTRACT

Two-site immunometric assays for multideterminant antigens are described in which the antigen is reacted with an immobilized monoclonal antibody directed against one antigen determinant and a second monoclonal antibody that is directed against a distinct antigenic determinant and is of a different class or subclass than the immobilized monoclonal antibody. The second monoclonal antibody is labeled in direct versions of the assay and is reacted with a labeled antibody against it in indirect versions of the assay. The immobilizing medium and classes (subclasses) of the antibodies may be selected so as to reduce the likelihood of nonspecific binding enhance sensitivity and/or permit signal amplification.

16 Claims, 1 Drawing Figure

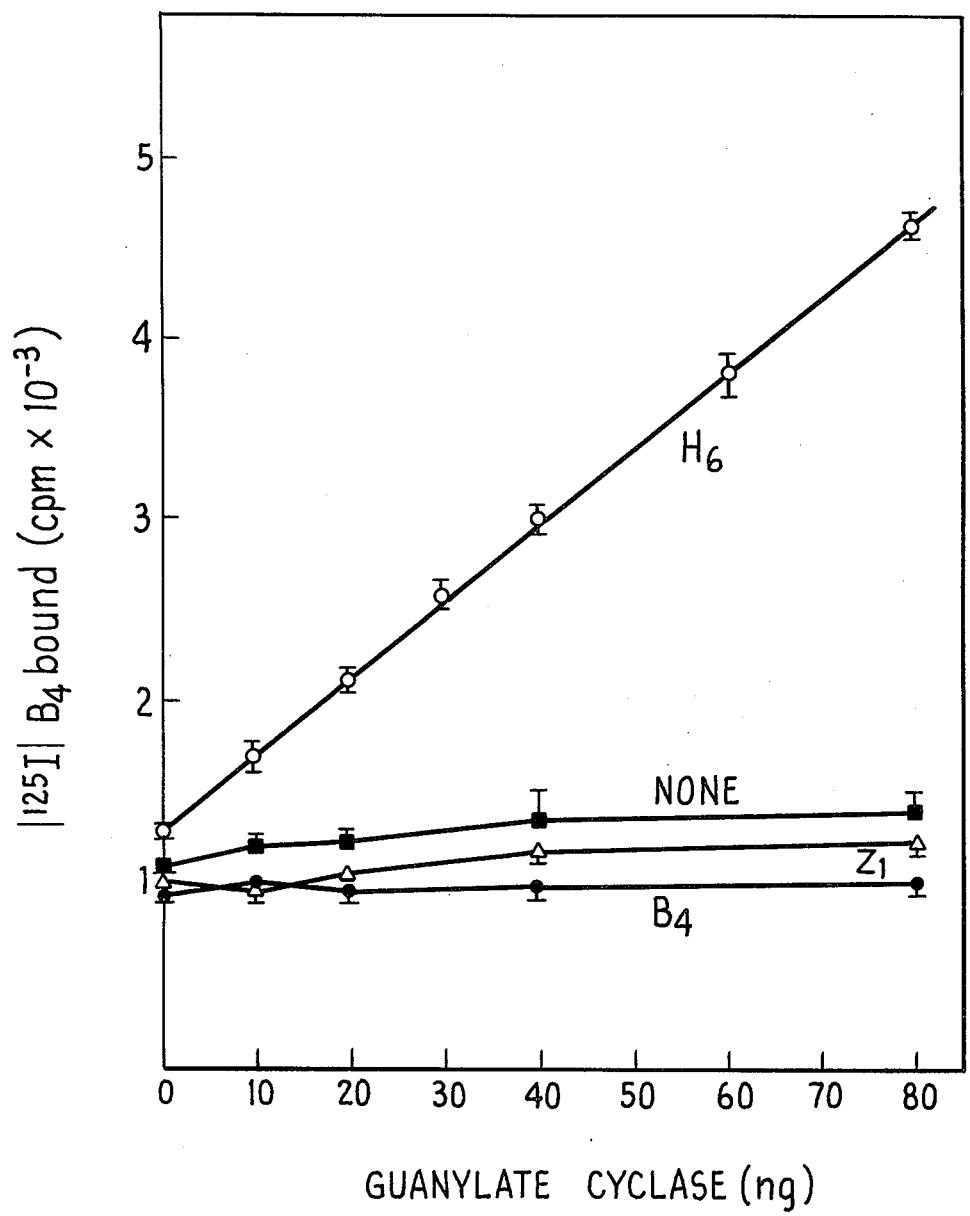

TWO-SITE IMMUNOASSAYS USING MONOCLONAL ANTIBODIES OF DIFFERENT CLASSES OR SUBCLASSES AND TEST KITS FOR PERFORMING SAME

REFERENCE TO GOVERNMENT GRANT

The invention described herein was made in the course of work under grants from the National Institutes of Health.

DESCRIPTION

1. Technical Field

The invention is in the field of immunoassays. More particularly, it relates to the field of two-site immunoassays for multideterminant antigens that employ monoclonal antibodies against distinct determinants.

2. Background Art

Two-site immunometric assays are well known. They are used to detect the presence or concentration of a multideterminant antigen in a liquid sample. They involve reacting the antigen with both an immobilized antibody directed against one of the antigenic determinants and an antibody that is directed against another of the antigenic determinants and is indirectly or directly labeled to permit detection of the resulting immune complex. The *Handbook of Radioimmunoassay* (1977) pp 131–154 and *Methods in Enzymology* (1980) 70:334–355 describe the most common variation of the two-site immunoassay, sometimes called the "forward two-step" method. In the forward two-step variation described in these references the sample is incubated with immobilized polyclonal antisera. Immobilized complexes are separated from the incubation mixture and incubated with labeled polyclonal antisera. U.S. Pat. No. 4,098,876 describes another variation of the two-site immunometric assay called the "reverse two-site" method. In the reverse two-site method the sample is incubated with the labeled antisera first, followed by incubation with the immobilized antisera. There is also a third version of the assay in which all three reactants are incubated simultaneously.

The use of monoclonal antibodies in all three versions of the two-site immunometric assay is described in *Clin Chem* (1981) 27/11:1797–1806, Belgian Pat. No. 889,855, and French Pat. Appln. No. 8115030 (Publication No. 2487983).

It is known that IgG1 and IgG2 bind to protein A (a cell wall component of stapylococci) with different affinities and that IgG1 can be selectively eluted from protein A at a selected pH. *Immunochemistry* (1978) 15:429–436. The use of a monoclonal IgG2 immobilized on protein A membrane to precipitate microsomal PGH Synthase is reported in *J Biol Chem* (1981) 256:10375–10382.

A principal object of the present invention is to provide an improved two-site immunoassay using monoclonal antibodies in which the likelihoods of nonspecific binding of the directly or indirectly labeled antibody to the immobilizing material and, in the case of indirect versions of the assay, the nonspecific binding of labeled moieties to the immobilized antibody are reduced. This improved assay is particularly useful in assays for detecting very low levels of antigen where such nonspecific binding would give an unacceptable detection limit or unacceptable levels of false-positive results.

DISCLOSURE OF THE INVENTION

One aspect of the invention is an improvement in a two-site immunometric assay for detecting a multideterminant antigen in a sample in which the antigen is reacted with (1) an immobilized monoclonal antibody against one of the determinants of the antigen and (2) a directly or indirectly labeled monoclonal antibody against another distinct determinant of the antigen. The improvement comprises using monoclonal antibodies of different classes or subclasses for the immobilized antibody and the labeled antibody.

Another aspect of the invention is a test kit for carrying out the direct version of the above described assay comprising:
  (a) an immobilized monoclonal antibody directed against one of the determinants of the antigen; and
  (b) a second monoclonal antibody that is
    (i) directed against another distinct determinant of the antigen;
    (ii) is labeled; and
    (iii) is of a different immunoglobulin class or subclass than the immobilized monoclonal antibody.

Test kits for indirect versions include an unlabeled second antibody and a third labeled antibody directed specifically against the second monoclonal antibody.

BRIEF DESCRIPTION OF THE DRAWING

The drawing is a graph depicting the result of the assays described in the example, infra.

MODES FOR CARRYING OUT THE INVENTION

The sample that may be assayed according to the invention is any liquid or biological sample that contains or is suspected of containing the multideterminant antigen whose presence or concentration is to be determined. Human or animal body fluids such as blood serum, cerebrospinal fluid, amniotic fluid, urine, and tissue extracts will usually be involved. Most body fluids may be stored frozen if it is impractical or inconvenient to carry out the assay on freshly procured sample. Preliminary extraction procedures or other special precautions may be required with samples if the antigen is labile, liable to aggregate, or has a tendency to be absorbed by the storage container.

The antigens that may be assayed according to the invention technique are multideterminant antigens. Such antigens have two or more antigenic determinants (epitopes) that are distinct (not identical) immunologically and whose sites are such that complementary antibodies may recognize and bind to them. The term "antigen" as used herein is intended to include both immunogenic entities (entities that elicit an immune response) as well as entities (haptens) that are recognized and bound by antibodies but do not elicit an immune response. Antigens present in body fluids include cells, enzymes, proteins, peptides, cell surface antigens and other cellular components, differentiation antigens, lymphokines, growth factors, hormones, drugs, toxins, viruses bacteria and other pathogens. Specific examples of multideterminant antigens for which two-site assays have been used are hepatitis-associated antigen, thyroid stimulating hormone, carcinoembryonic antigen, parathyroid hormone, nerve growth factor, human growth hormone, tetanus toxin, albumin, ovalbumin, X antigen, ferritin, GFA protein, S-100 protein, alpha-fetoprotein, antithymocyte globulin, blood coagulation factor VIII, γ chain of hemoglobin F, follicle-stimulating hormone, and human chorionic gonadotropin.

Monoclonal antibodies of different classes or subclasses directed against distinct determinants of multideterminant antigens of interest may be made by the somatic cell hybridization technique first reported by Kohler, G. and Milstein, C. *Nature* (London) (1975) 256:495–497. This technique uses antibody-producing cells, eg spleen or lymphoid cells, from a host animal, preferably a mouse, immunized with the antigen as one of the hybridization partners and an appropriate selectable cancer (myeloma) cell line as the other hybridization partner. The antibody-producing cells are hybridized (fused) with the tumor cells using a fusogen such as polyethylene glycol having a Mw of 1,000 to 6,000 daltons. A myeloma cell line that is sensitive to a selective medium such as HAT medium (Littlefield, *Science* (1969) 145:709–710), fuses efficiently, and will support stable high level expression and secretion of antibody by its hybridization partner is used. While myeloma cells from any species may be used, murine myeloma lines having these characteristics are available currently and are preferred. Examples of such lines are those derived from the original MOPC-21 and MPC-11 mouse tumors that are available from the Salk Institute Cell Distribution Center, PO Box 1809, San Diego, Calif. 92112. A myeloma cell:antibody-producing cell ratio in the range of about 1:10 and about 10:1 will normally be used. The individual cell concentrations will typically be in the range of about $10^6$ to $10^8$, preferably $1 \times 10^7$ to $5 \times 10^7$, cells/ml fusion medium. Balanced salt solutions containing about 30% to 60% (w/v), preferably 35% to 50% (w/v), fusogen may be used as a fusion medium. After the fusion, the cells are washed with fusogen-free medium to remove fusogen. They are then seeded and cultivated in the selective medium to eliminate unhybridized parent cells and leave only hybrids that are resistant to the selective medium and possess the immortality of the myeloma parent. The cultivation will normally take about three to five weeks.

Surviving hybridomas may be examined for production of antibody against the antigen by immunoassay. Positive clones that produce antibodies that bind to distinct determinants of the antigen may be selected by incubating the antigen first with unlabeled antibody from one of the clones and then with labeled antibody from another clone and observing whether binding of the labeled antibody was blocked by binding of the unlabeled antibody. The antibodies may be characterized by class and subclass by known serologic or chemical techniques. In this regard there are five classes of immunoglobulin, IgG, IgA, IgM, IgD and IgE which are distinguished by structural differences in the constant regions of their heavy chains. The IgG class is subdivided into four subclasses IgG1, IgG2, IgG3, and IgG4 again based on serologic or physiochemical differences in the constant region of the heavy chain. The IgM and IgA classes are each similarly divided into two subclasses. Monovalent (Fab, Fab') or divalent (F(ab')$_2$) fragments of the second (labeled) monoclonal antibody may be used. Such fragments may be made by digesting the monoclonal antibody with appropriate enzymes and isolating the desired fragment from the digest. Accordingly, as used herein the term "antibody" as applied to the second (labeled) monoclonal antibody is intended to include whole immunoglobulin as well as antigen binding fragments thereof.

The hybridoma clones that produce the antibodies of desired specificity, affinity, and class may be subcloned by limiting dilution techniques and grown in vitro or in vivo by known techniques. The monoclonal antibody secreted by the subclones may be separated from the culture medium or ascites fluid or serum when grown in vivo by known techniques such as ammonium sulfate precipitation, DEAE cellulose chromatography, or affinity chromatography. Further purification of the antibodies, if desired, may be achieved by ultracentrifugation and microfiltration.

The immobilized monoclonal antibody used in the invention assay is made by chemically or physically attaching the monoclonal antibody to an essentially water insoluble surface, matrix, or body. In the immunoassay art antibody immobilizing materials are sometimes called "carriers" or "supports". Examples of such media are natural materials such as protein A membranes, cellulose, and agarose and synthetic materials such as Sephadex, cross-linked polysaccharides, polyvinylchloride, polypropylene, polystyrene, and the like. The media may be in various forms such as surfaces, particles, porous matrices, and the like. Methods for covalently or physically attaching the antibody to such immobilizing media are well known.

In some instances it may be desirable to immobilize the monoclonal antibody via a linking antibody (monoclonal or polyclonal) against the antibody to be immobilized. In these instances the antibody against the monoclonal antibody would be attached to the immobilizing material before the monoclonal antibody is incubated with the material.

It will be appreciated that the assay may employ an immobilized monoclonal antibody that has been prepared beforehand or the immobilization may be done in situ as a step of the assay.

Directly labeled monoclonal antibodies for use in the invention may be labeled with a label that provides the desired signal type and intensity by known methods. The nature of the label is not critical. Examples of labels that may be used are isotopic labels such as $^{125}$I, $^3$H, $^{14}$C, fluorescent labels such as fluorescein isothiocyanate and rhodamine, chemiluminescent labels such as luciferin, enzyme labels such as biotin-avidin and horseradish peroxidase, spin labels, and bacteriophage labels. In indirect assays labeled antisera against the second monoclonal antibody are employed. A similar diversity of labeling techniques could be used for labeling the antisera for use in the indirect assay. The present invention is especially advantageous in indirect assays and permits substantial amplification of the signal without attendant increase in the level of background signal due to nonspecific binding. In this regard the use of a second monoclonal antibody of a different class or subclass allows one to employ the second monoclonal antibody as a site for binding one or more ligands that bind to the second monoclonal antibody but do not recognize the first monoclonal. Amplification is effected by binding a multiplicity of labeled ligands to the second antibody or by using ligands that act catalytically. Such amplification permits the detection of very small amounts of antigen because the initial ternary immobilized complex is used as a site to bind large amounts of label or ligands that act catalytically. In this regard it is within the scope of this invention to bond one or more nonlabeled ligands to the initial ternary complex before binding the final labeled ligand to the multilayer complex. The use of such intermediate layers of ligands may permit even greater signal amplification and/or specificity.

The incubation conditions (time, temperature, pH, reagent concentrations, etc) that are used in the prior art two-site assays may be used in the invention assay. Similarly the reagent addition sequences, separation (wash) procedures and other methodology generally follow the prior art procedures. However, the use of different classes or subclasses of monoclonal antibodies permits improved removal of non-specifically bound labeled antibody from the complex. This improvement is achieved by employing an immobilizing medium from which antibodies of the class or subclass of the labeled monoclonal antibody may be removed selectively from the immobilizing medium without substantial removal of antibodies of the class or subclass of the original immobilized monoclonal antibody.

The incubations of the assay will be carried out under conditions that favor binding between the antigen and the immobilized monoclonal antibody and between the resulting immobilized immune complex and the labeled monoclonal antibody in the forward two-step technique and vice versa in the reverse two-step method. Temperatures, pH and duration are the most important process conditions in the incubation. Reduced temperatures, eg 0° C. to 25° C., will typically be used in binding the first monoclonal antibody to the immobilizing medium. The incubation with antigen and labeled antibody may be done at temperatures in the range of 0° C. and 40° C. Room temperature is used for convenience. The pH will normally be about 6 to 9, preferably about 7, and the binding reaction will usually reach equilibrium in about 10 min to 2 days, depending upon the particular antibodies and antigen involved. Antibody will normally be used in excess. In the forward two-step method the insolubilized monoclonal antibody may be incubated simultaneously with the antigen and labeled reagent. After incubation with the labeled reagent and antigen the resulting insoluble incubation product is separated from the liquid and treated (eg, washed) under such conditions that selectively remove non-specifically bound labeled monoclonal antibody. For instance when protein A membranes or protein A bound to synthetic carrier are used as an immobilizing medium nonspecifically bound second antibody may be selectively removed from the protein A by washing at a suitable pH, eg,

| First Monoclonal Antibody | Second Monoclonal Antibody | Wash pH |
|---|---|---|
| IgG2a | IgG1 | 6 |
| IgG2a | IgM | 6–7 |
| IgG2b | IgG1 | 4+ |
| IgG2b | IgM | 4+ |

Following this final separation further processing steps may be required depending upon whether the assay is an indirect assay and the nature of the label. In indirect assays the additional step of reacting the incubation product with labeled antisera is required. With some labels, such as enzyme labels, the product must be reacted with a suitable substrate or ligand to make the product detectable.

The final step in the assay is detecting the labeled complex. The particular detection technique employed will depend upon the nature of the label, eg, radiation counting with isotopic labels, fluorescent intensity with fluorescent labels, spectrophotometric detecting with enzyme labels, and the like. The result of the assay will typically be interpreted by comparing it with a standard curve or with control results.

The following example further illustrates the two-site immunometric assay of the invention. This example is not intended to limit the invention in any manner. The example concerns a two-site immunoradiometric assay for guanylate cyclase. The methods and materials employed in it were as follows.

PURIFICATION OF SOLUBLE GUANYLATE CYCLASE

Soluble guanylate cyclase was purified from a $105,000 \times g$ supernatant fraction of rat lung as described by Lewicki, J. A., et al., *J Cyc Nuc Res* (1981) 6:283–296. Briefly, the scheme included isoelectric (pH 5.0) and ammonium sulfate (20%–50%) precipitations, chromatography on guanosine 5'-triphosphate (GTP)-agarose, and preparative electrophoresis on a 7% polyacrylamide gel. The purity of the preparations was assessed by the specific activity determinations (250–400 nmoles cyclic guanosine 5'-monophosphate (cGMP) formed/min/mg protein with $Mn^{2+}$ -GTP; 30–60 nmoles/min/mg with $Mg^{2+}$ -GTP) and the presence of a single protein band with analytical polyacrylamide gel electrophoresis in the presence of sodium dodecyl sulfate. Purified guanylate cyclase is 150,000 daltons and has two subunits of 72,000 daltons. Purified enzyme was used to immunize mice for monoclonal antibody production and as a standard in the direct immunoradiometric assay described below.

GUANYLATE CYCLASE ACTIVITY DETERMINATIONS

Guanylate cyclase activity was determined by incubating enzyme at 37° C. in Tris-HCl (50 mM, pH 7.6), containing 0.02% bovine serum albumin, 4 mM $MnCl_2$ (or $MgCl_2$), and 1 mM GTP. In crude enzyme preparations, theophylline (10 mM), creatine phosphate (7.5 mM), and creatine phosphokinase (14 μg; 135 units/mg) were included in the reaction mixtures. Incubations were terminated by adding cold sodium acetate (50 mM, pH 4.0) and heating at 90° C. for three minutes. Generated cyclic GMP was measured by radioimmunoassay as described by Steiner, A., et al., *J Biol Chem* (1972) 247:1106–1113.

PREPARATIONS OF MONOCLONAL ANTIBODIES TO SOLUBLE GUANYLATE CYCLASE

Monoclonal antibodies to soluble guanylate cyclase were produced by the somatic cell hybridization technique according to Brandwein, H. J., et al,. *PNAS* (1981) 78:4241–4245. Briefly, Balb/c or A/J×C57B1 mice (Jackson Labs) were injected several times at monthly intervals with 3–7 μg of purified soluble guanylate cyclase from rat lung. Four days following the final immunization, the mice were sacrificed, spleens removed and fused to SP 2/0 myeloma cells, using polyethylene glycol as the fusogen (Koch-Light 1000). Following the selection of hybridomas with hypoxanthine-aminopterin-thymidine media, hybridomas secreting specific anti-guanylate cyclase antibody were identified with an immobilized enzyme plate coat assay. In this procedure, 10–100 ng of purified soluble guanylate cyclase were bound to individual wells of polyvinyl chloride microtiter plates. Nonspecific binding of antibody to the plates was diminished by treating wells with 20% IgG-free horse serum, following exposure to the enzyme. After washing the plates extensively with 1% IgG-free horse serum, media from the secreting hybridomas was added to the plates. Specifically bound anti-guanylate cyclase antibody was detected by adding [$^{125}$I]-rabbit anti-mouse IgG. In control wells, 20 mM Tris, pH 7.6, was added in place of guanylate cyclase. Following identification of positive clones, cells were subcloned several times to ensure their monoclonal nature, then grown in mass culture and injected into Balb/c mice, intraperitoneally, to produce antibody-rich ascitic fluid. Among the monoclonal antibodies prepared from positive clones was one designated B$_4$ and another designated H$_6$. Samples of the clones that produce B$_4$ and H$_6$ were deposited at the American Type Culture Collection, 12301 Parklawn Drive, Rockville, Md. 20852 on or about Feb. 15, 1983 and have been assigned the ATCC numbers HB-8212 and HB-8211, respectively.

Monoclonal antibodies B$_4$ and H$_6$ were purified to apparent homogenity on Protein A-Sepharose columns (Pharmacia), according to the procedure of Ey, P. L., et al., *Immunochemistry* (1978) 15:429–436. Ascitic fluid was applied to columns in 100 mM phosphate buffer, pH 8.2 (flow rate=15 ml/hr). Columns were washed with 50-100 ml of the same buffer. Antibodies were eluted, successively, with 50 mM citrate buffer at pH 6.0 (elutes IgG1 subclass antibodies), pH 4.5 (elutes IgG2a) and pH 3.0 (elutes IgG2b). The elutions indicated that B$_4$ was an IgG1 and that H$_6$ was an IgG2a. The subclasses of B$_4$ and H$_6$ were confirmed by Ouchterlony immunodiffusion using subclass specific rabbit anti-mouse immunoglobulins. In control experiments, antibody Z$_1$, a monoclonal antibody (IgG2a) not directed to guanylate cyclase, was purified as described above.

Samples of monoclonal antibodies B$_4$ and H$_6$ were iodinated using the immobilized lactoperoxidaseglucose oxidase technique described by David, G. A. and Reisfeld, R. A., *Biochemistry* (1974) 13:1014–1021. In this procedure, 100 μg of the purified antibodies were incubated with Enzymobeads (Bio-Rad), Na$^{125}$I (1 mCi), KI (100 μM), and phosphate buffer, pH 7.2 (100 mM) in a total volume of 100 microliters. The reaction was initiated by adding a β-D glucose (25 μl of a 1% solution) and proceeded for twenty minutes at room temperature. The reaction was stopped with cold NaN$_3$ (100 mM). Protein-bound and free iodide were separated by chromatography on Sephadex G-25 gel in the presence of 1% IgG-free horse serum. The specific activity of the iodinated antibodies was routinely about 1 μCi/μg protein. The iodinated antibodies were stable when stored at −20° C. for up to four weeks.

The determinant specificity of antibodies B$_4$ and H$_6$ was determined by incubating iodinated H$_6$ with guanylate cyclase preadsorbed to polyvinyl chloride plates in the presence of unlabeled B$_4$ and vice versa. Neither unlabeled species blocked binding of the labeled species of the other to the enzyme. Therefore B$_4$ binds to a site on soluble guanylate cyclase distinct from the site recognized by H$_6$. This conclusion was confirmed by competitive binding and immunoprecipitation studies.

IMMUNORADIOMETRIC ASSAY FOR THE DIRECT DETERMINATION OF GUANYLATE CYCLASE CONCENTRATIONS

Ten grams of washed Staph aureus membranes (Pansorbin, Calbiochem) were mixed with 300 μg of purified monoclonal antibody H$_6$ in 50 mM Tris, pH 7.6, 1% Tween 20 surfactant, containing 0.025% bovine serum albumin (total voluume=100 ml). The samples were incubated overnight at 4° C. Following this incubation, unbound H$_6$ antibody was removed by aspiration and the membrane-antibody complex was washed two times with 50 mM Tris buffer (pH 7.6) and 1% Tween 20 surfactant in the absence of bovine serum albumin. The antibody H$_6$-treated membranes were stored, at 4° C., as a 10% suspension in the same buffer, containing 0.02% sodium azide. Preparations were stable for at least four weeks.

Fifty μl of the 10% suspension of membrane-antibody H$_6$ complexes were incubated with 50 μl of purified guanylate cyclase standards, or crude samples, and 20,000-30,000 cpm of [$^{125}$I]-B$_4$, overnight, to ensure equilibrium conditions. Three ml of 50 mM citrate buffer, pH 6.0, containing 1% Tween-20 surfactant, were added to each tube to remove [$^{125}$I]-B$_4$ which was non-specifically absorbed to the Staph aureus membranes. Since B$_4$ is an IgG1 subclass immunoglobulin and H$_6$ is an IgG2a, only adsorbed B$_4$ was removed by this washing procedure. Mouse IgG2a antibodies remain bound to Staph aureus above pH 4.5. Samples were then centrifuged at 2,300 rpm in a Beckman TJ-6 centrifuge and supernatant fractions were removed by aspiration or decantation. Pellets were monitored by gamma counting. For standard curves, 10-100 ng of purified guanylate cyclase was added to standard tubes. Comparison assays were run in which H$_6$ was replaced with B$_4$, Z$_1$ or no atibody. All samples were assayed in duplicate or triplicate and mean values from representative experiments were determined. The results of these assays are shown in the drawing in which the open circles represent the results where H$_6$ was bound to the Staph aureus membranes, the solid circles those where H$_6$ was replaced with B$_4$, the open triangles those where H$_6$ was replaced with Z$_1$, and the solid rectangles those where H$_6$ was replaced with no antibody.

As seen in the drawing the amount of [$^{125}$I]-B$_4$ bound was linear over a range of guanylate cyclase concentrations (r=0.991). While the sensitivity and range of the assay varied with the age of the [$^{125}$I]-B$_4$ antibody, the assay was typically linear over a range of 10-100 ng of guanylate cyclase. The slope of the curve with higher concentrations of enzyme decreased (not shown).

The reported tests also demonstrated that the measurement of guanylate cyclase protein is dependent on the use of the antibodies B$_4$ and H$_6$ in the sequence described. No [$^{125}$I]-B$_4$ binding was detected when Staph aureus membrane-B$_4$, Staph aureus membrane-Z$_1$ or Staph aureus membranes alone were used. Specific binding was seen only upon using Staph aureus membrane-H$_6$ complexes. This demonstrates the specificity of the method and, further, indicates that there is little or no non-specific binding of [$^{125}$I]-B$_4$ or guanylate cyclase to Staph aureus-antibody complexes.

Numerous control experiments were run to assess the validity of the assay. For example, the standard curve was run in the presence and absence of a crude rat lung supernatant fraction containing a premeasured amount of guanylate cyclase protein. Addition of the crude lung supernatant did not alter the slope of the standard curve (not shown). More importantly, the amount of enzyme measured in the presence of the crude supernatant was in good agreement with that predicted by summing each standard with the assayed amount of guanylate cyclase present in the crude supernatant fraction. These experiments demonstrate the applicability of the assay to measuring guanylate cyclase in crude tissue extracts.

The test kits for carrying out the direct two-site immunoassays of the invention will include either an immobilizing medium plus the first monoclonal antibody or preimmobilized first monoclonal antibody and labeled second monoclonal antibody. Kits for carrying out indirect immunoassays will include the immobilizing medium plus first monoclonal antibody or preimmobilized first monoclonal antibody, unlabeled second monoclonal antibody, and labeled antibody against the second monoclonal antibody. Suitable quantities of these reagents will normally be packaged individually in appropriate containers. In addition to these main components the kits will typically include buffers control or standard reagents, instructions, and depending upon the nature of the label involved, reactants that are required to produce a detectable product. These kits may be produced and packaged using conventional test kit manufacturing procedures.

Modifications of the above described modes for carrying out the invention that are obvious to those of skill in immunodiagnostics, medicine and related fields are intended to be within the scope of the following claims.

We claim:

1. In a two-site immunoassay for detecting the presence of a multideterminant antigen in a sample wherein the antigen in the sample is reacted with
   (a) an immobilized monoclonal antibody directed aganist one of the antigen determinants; and
   (b) a second monoclonal antibody that is
      (i) directed against another distinct determinant of the antigen; and
      (ii) labeled directly or indirectly; the improvement wherein the second monoclonal antibody is of a different immunoglobulin class or subclass than the immobilized monoclonal antibody.

2. The immunoassay of claim 1 wherein the second monoclonal antibody is of a class or subclass of antibody that may be removed selectively from the immobilizing medium to which the immobilized monoclonal antibody is attached without substantial removal of the immobilized antibody from the immobilizing medium.

3. The immunoassay of claim 1 wherein the immobilized monoclonal antibody is immobilized by Protein A.

4. A direct two-site immunoassay for detecting the presence of a multideterminant antigen in a sample comprising:
   (a) incubating the sample with an immobilized first monoclonal antibody against one of the antigen determinants;
   (b) incubating the incubation product of (a) with a labeled second monoclonal antibody against another distinct determinant of the antigen, the second monoclonal antibody being of a different immunoglobulin class or subclass than the first monoclonal antibody; and
   (c) detecting the presence of labeled complex in the incubation product of (b).

5. The immunoassay of claim 4 wherein the second monoclonal antibody is of a class or subclass of antibody that may be removed selectively from the immobilizing medium to which the immobilized monoclonal antibody is attached without substantial removal of the immobilized antibody from the immobilizing medium.

6. The immunoassay of claim 6 wherein the immobilized monoclonal antibody is immobilized by Protein A.

7. The immunoassay of claim 6 wherein after (b) and before (c) the protein A complexes are separated from the incubation mixture of (b) and washed with an aqueous medium having a pH that selectively removes nonspecifically bound second monoclonal antibody from the protein A complexes.

8. An indirect two-site immunoassay for detecting the presence of a multideterminant antigen in a sample comprising:
   (a) incubating the sample with an immobilized first monoclonal antibody against one of the antigen determinants;
   (b) incubating the incubation product of (a) with a second monoclonal antibody against another distinct determinant of the antigen, the second monoclonal antibody being of a different immunoglobulin class or subclass than the first monoclonal antibody;
   (c) incubating the incubation product of (b) with labeled antibody against the second monoclonal antibody; and
   (d) detecting the presence of labeled immobilized complexes in the incubation product of (c).

9. The immunoassay of claim 8 wherein the second monoclonal antibody is of a class or subclass of antibody that may be removed selectively from the immobilizing medium to which the immobilized monoclonal antibody is attached without substantial removal of the immobilized antibody from the immobilizing medium.

10. The immunoassay of claim 8 wherein the immobilized monoclonal antibody is immobilized by Protein A.

11. A test kit for carrying out a direct two-site immunoassay for detecting the presence of a multideterminant antigen in a sample comprising in containers:
    (a) an immobilized monoclonal antibody directed against one of the determinants of the antigen; and
    (b) a second monoclonal antibody that is
       (i) directed against another distinct determinant of the antigen;
       (ii) is labeled; and
       (iii) is of a different immunoglobulin class or subclass than the immobilized monoclonal antibody.

12. The test kit of claim 11 wherein the second monoclonal antibody is of a class or subclass of antibody that may be removed selectively from the immobilizing medium to which the immobilized monoclonal antibody is attached without substantial removal of the immobilized antibody from the immobilizing medium.

13. The test kit of claim 12 wherein the immobilized monoclonal antibody is immobilized by Protein A.

14. A test kit for carrying out a direct two-site immunoassay for detecting the presence of a multideterminant antigen in a sample comprising in containers:
    (a) a first monoclonal antibody directed against one of the determinants of the antigen;
    (b) a first monoclonal antibody immobilizing medium; and
    (c) a second monoclonal antibody that is
       (i) directed against another distinct determinant of the antigen;
       (ii) is labeled; and
       (iii) is of a different immunoglobulin class or subclass than the first monoclonal antibody.

15. Test kit for carrying out an indirect two-site immunoassay for detecting the presence of a multideterminant antigen in a sample comprising in containers:
(a) an immobilized monoclonal antibody directed against one of the determinants of the antigen;
(b) a second monoclonal antibody that is
 (i) directed against another distinct determinant of the antigen;
 (ii) is of a different immunoglobulin class or subclass than the immobilized monoclonal antibody; and
(c) a labeled antibody against the second monoclonal antibody.

16. A test kit for carrying out an indirect two-site immunoassay for detecting the presence of multideterminant antigen in a sample comprising in containers:
(a) a first monoclonal antibody directed against one of the determinants of the antigen;
(b) a first monoclonal antibody immobilizing medium;
(c) a second monoclonal antibody that is
 (i) directed against another distinct determinant of the antigen;
 (ii) is of a different immunoglobulin class or subclass than the first monoclonal antibody; and
(d) a labeled antibody against the second monoclonal antibody.

* * * * *